United States Patent [19]

Jacob

[11] Patent Number: 4,606,354

[45] Date of Patent: Aug. 19, 1986

[54] GOLD COATED CARBON IMPLANT AND METHOD OF TREATING ARTHRITIS THEREWITH

[76] Inventor: Ezekiel J. Jacob, 25 Monroe Pl., Brooklyn, N.Y. 11201

[21] Appl. No.: 736,562

[22] Filed: May 21, 1985

[51] Int. Cl.⁴ .......................... A61N 1/00; A61N 1/30
[52] U.S. Cl. .................................. 128/784; 128/1.1; 604/20; 427/2; 428/367; 428/389
[58] Field of Search ............... 128/1.1, 1.2, 1.3, 68.1, 128/389, 391, 392, 419 R, 419 F, 787–789, 92 G, 335.5, 339, 783, 784; 604/20, 265, 21; 427/2; 428/389, 375, 367, 408

[56] References Cited

U.S. PATENT DOCUMENTS

| 527,037 | 10/1894 | Funk | 128/787 X |
|---|---|---|---|
| 2,069,112 | 1/1937 | Oppenheim | 128/787 |
| 3,477,436 | 11/1969 | Sawyer | 128/335.5 |
| 4,027,393 | 6/1977 | Ellis | 604/20 |
| 4,292,968 | 10/1981 | Ellis | 604/20 |
| 4,405,311 | 9/1983 | Greatbatch | 128/419 R |
| 4,411,648 | 10/1983 | Davis | 604/21 |
| 4,506,673 | 3/1985 | Bonnell | 128/784 |

FOREIGN PATENT DOCUMENTS

| 3228849 | 2/1984 | Fed. Rep. of Germany | 604/265 |
|---|---|---|---|
| 367862 | 4/1963 | Switzerland | 128/391 |

Primary Examiner—Clifford D. Crowder

[57] ABSTRACT

An implant for the treatment of the pain of arthritis which comprises a carbon fiber which has a discontinuous coating of gold thereon, exposing the carbon in patches. The carbon and gold form a galvanic couple which is implanted in an arthritic joint and in the presence of body fluids acts like a battery and released gold ions continuously, thus relieving pain.

2 Claims, 3 Drawing Figures

GOLD COATED CARBON IMPLANT AND METHOD OF TREATING ARTHRITIS THEREWITH

PRIOR ART

U.S. Pat. No. 4,405,311 "METHOD AND APPARATUS FOR DIRECT ELECTRICAL INJECTION OF GOLD IONS INTO TISSUE SUCH AS BONE" Sept. 20, 1983.

"DRUG THERAPY IN RHEUMATOID ARTHRITIS"—JANNUZZI et. al. New England Journal of Medicine Vol 309, No. 17 pages 1023 f.f. which includes 52 references and citations pages 1027-1028.

BACKGROUND OF THE INVENTION

The Arthritis Foundation estimates (1985) the number of persons afflicted with arthritis in the U.S. is 37 Million. About 2 to 10 billion dollars are spent in "cures" in each year.

Gold, however, is a valid answer.

Quoting from the Jannuzzi article: "Does Drug Therapy slow radiographic deterioration in Rheumatoid Arthritis?" The abstract says; "We found evidence suggesting that both gold and cyclophosphamide can RETARD radiographic progression of joint destruction". In a placebo-controlled prospective trial it was reported for the first time that gold slowed radiographic progression of joint damage, See Sigler et al "Gold Salts in the treatment of rheumatoid arthritis—A double Blind Study", Annals of Internal Medicine, 1974, 80:21-6. Gold salts are a systemic poison, and have toxic side effects. Treatment has to be discontinued in 6 months to a year. The efficacy of gold is supported in a report of the Cooperation Clinics Committee of the American Rheumatism Association: "A controlled trial of gold salt therapy in rheumatoid Arthritis"-"Arthritis/Rheum" 1973, 16:353-8.

DELIVERY OF GOLD IONS BY IMPLANT

An implant of gold wire complete with a battery and an electrical circuit in size about one inch × ¼ × ¼ inch is inserted into the arthritis joint. This is in the prior art as U.S. Pat. No. 4,405,311. The drawbacks are:

The gold wire stretches and is flattened out by the weight and torsion of the joint.

The gold wire by itself cannot generate gold ions. The gold wire has to be powered by an electrical circuit consisting of a battery, and a constant current generator, and all these components are encapsulated in an epoxy material which in turn is coated with a silicone medical adhesive. The entire implant is of considerable size, one inch by ¼ by ¼". Insertion and implantation into small joints, such as the finger joint or as an extreme case, the Temporal Mandibular Joint (TMJ) are impossible. Furthermore, the implant must be removed surgically when the battery runs down and has to be replaced. However the implant of U.S. Pat. No. 4,405,311 does indeed concentrate the gold at the arthritic joint, and avoids raising the systemic level of gold to prevent side effects.

THE PROGRESSION TO THE GOLD CONTAINING ARTHRITIS IMPLANT

Starting with the proved efficacy of gold salts, orally or injectably administered, the progression has been to the delivery of gold ions from a gold wire implant-system comprising a battery, a constant current generator and a housing resulting in a big 1"×0.250" tissue implant, massive in size compared to the accomodation available within a body-joint. The gold containing arthritis implant of this invention is a novel step forward, for these reasons:

a. It comprises single carbon fibers coated with gold.

b. The core fiber makes the gold containing implant dimensionally stable as regards inextensibility. It cannot be stretched. It cannot be flattened out by a load at the load bearing joint within which it has been implanted.

c. It is a galvanic couple generating gold ions by the mere presence of body fluids in the joint where it has been implanted. It requires no "power plant" to generate the gold ions, and the large "power plant" does not have to be surgically implanted, because the need for a "power plant" has been eliminated.

d. The delivery of gold ions from this gold containing implant is regulated by the electrolyte composition of the diseased joint, because this invention is a galvanic couple, and the movement of the ions from one member of the couple to another depends on the presence of an electrolytic fluid having electrical conductivity. The theory is stated here, without affecting the validity of the invention, that ion flow will be self regulated by the body electrolyte concentration at or near the diseased joint, and that electrolyte concentration will be increased as part of the body reaction, during the acute episodes of the disease, and during the progressive narrowing of joint space, thus providing gold ions in a body-demand related mode.

e. The extremely small size of the gold coated carbon fiber permits it to be used in a space as small as 10 microns by surgical implantation, as for example the small joints in the fingers, or more typically, the temporal mandibular joint.

IS GOLD PRODUCED FROM THE GOLD CONTAINING ARTHRITIS IMPLANT IN THE PRESENCE OF BODY SERUM? RESULT OF ONE YEAR IMMERSION TEST

The gold containing arthritis implant tested was a carbon fiber plated with gold, then chopped into strands. The chopped ends revealed a cross section with carbon as the core and Gold as the integument. Fiber, plated with gold was obtained from American Cyanamid Company, New York N.Y., Polymer Products Division, manufactured by their Electro-Metalloid Division, Irvingron N.Y.: Trade name as sold is: "CYCOM MCG FIBER ®". The Core fiber is a carbon fiber made of Graphite, or a graphite fiber. It has a tensile elongation of approx. 1%, and an ultimate strength of 320,000 pounds per square inch. Slight variations in tensile ultimate elongation would be acceptable, going perhaps to 10%.

A strand of fiber would constitute a galvanic couple at each end since the cross section shows an outer ring of Gold and an inner core of Carbon fiber and would constitute a gold-ion transfer mechanism when immersed in a conductive fluid.

CONDUCTIVE FLUID USED FOR IMMERSION TEST

A reference Serum Lot No. 1889B001 in TMA Bicarbonate-Glycerol Diluent Lot No. 1822B001. This is Bovine Serum sold for Automated Chemistry analytical procedures. Trade name is "Q-PAK ®" sold by Hyland Diagnostics Division of Travenol Laboratories Inc, Deerfield, ILL. 60015 U.S.A.

Serum fluid was mixed with 1% of its weight with chopped strands of Cycom MCG and 1% of glutaraldehyde to prevent putrefaction of the proteinaceous serum. Slurry was then left on the lab table for one year in a stoppered test tube. During the year at infrequent intervals, the test tube was vigorously shaken.

TEST FOR GOLD AT END OF YEAR 4 mls of liquid was isolated by filtration. On drying, this solution yielded 411.4 mgs of residue which was analysed by emission spectroscopy. Report of Lucius Pitkin Inc New York, N.Y. showed 0.00X% (where "X" is a number below 5.) Gold. Report is dated Feb. 21, 1985, Number 923514, titled: "AUREOUS JOINT IMPLANT". The Gold created within the serum by the galvanic action of the Gold-Carbon galvanic couple, is the function of the invention namely, a function of the gold containing Arthritis Implant, operating in a conductive bath, such as the serum.

DETAILED DESCRIPTION OF THE ILLUSTRATED EMBODIMENTS

EXAMPLE #1

This is the chopped length of a strand of gold coated carbon fiber.

This was the form tested for one year in the Lucius Pitkin Report #923514, as mentioned above.

This is the simplest form of the gold containing arthritis implant. The exposed cross-sectional area at each end of the fiber comprised an outer annular ring of gold material and within it was the central core of carbon fiber. Each exposed end, coacting with the serum in which it was immersed, constituted a galvanic couple, liberating gold ions.

EXAMPLE #2

Figure 1:
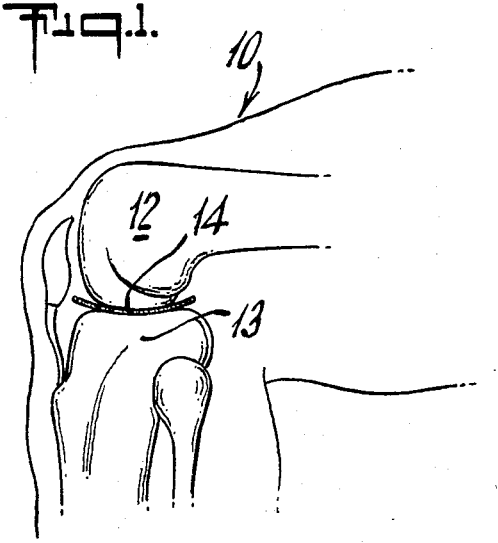
FIG. 1 is a view of the gold containing implant of the invention implanted in a knee joint.
Figure 2:
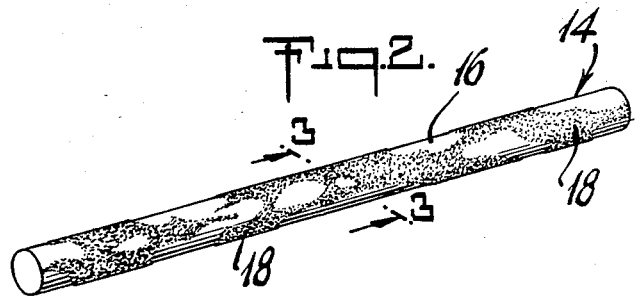
FIG. 2 is a preferred embodiment of the implant showing the discontinuous gold coating on a carbon fiber.
Figure 3:
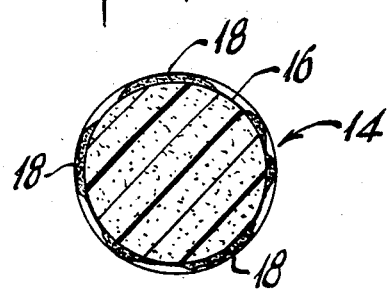
FIG. 3 is a cross sectional view along the line 3—3 of FIG. 2.

This is the erose form of the gold containing arthritis implant shown in FIG. 2, and cross-sectionally in FIG. 3. The outer gold coating is not continuous. The underlying core fiber of Carbon is exposed in patches. Ths embodiment shown is the preferred embodiment, because it exposes a great many galvanic couples along the surface of the implant 14, in addition to the ones at each end. Greater amounts of gold ions will be generated when immersed in the body fluids, then the implant which was tested and had only one galvanic couple at each end of the plated fiber, and no galvanic couples along the surface. The method of creating a discontinuous aureous coating on the core carbon fiber is within the capacity of anyone skilled in plating art. Illustrative, but not restrictive was the method of dissolving out parts of the surface by drops of aqua regia. Preferred is the method of ion-beam deposition of Gold on the Carbon fiber by discontinuous deposition. Ion Beam modification of materials for Industry is a known technology. See paper presented by P. Sioshansi April 9–13, 1984 at the International Conference on Metallurgical Coatings, San Diego CA. U.S.A. Publication Publication is attached.

EXAMPLE #3

The gold containing arthritis implant comprises a multiplicity of fibers, coated either entirely or in erose fashion as in Example #2. These fibers are woven, knitted, matted, or otherwise made into a matted sheet and in the sheet form is implanted surgically in the diseased joint. A discontinuous application of a silicone medical adhesive is applied to or through the fibrous mat, discontinuity securing greater galvanic action after implantation.

EXAMPLE #4

The gold coating 18 is radioactive, or the entire gold containing implant is radioactive. Radioactivity is created by bombardment with gamma irradiation in a U.S. Govt. Reactor Facility, or alternatively the gold coating is created by plating in a bath of radioactive gold, or by ion-beam implantation using radioactive gold, or the core carbon fiber could be radioactive. A short half-life isotope is preferred. The benefits expected from this example is the benefit achieved by a treatment called "RADIATION SYNOVECTOMY" performed since 1981 under the direction of Dr. Clement Sledge at Harvard Medical School. News Report from N.Y. Daily News states: (Mar. 13, 1985)

""HOT" Shots to knees seen as Rx to arthritis victims" Boston, (AP): Injecting short-lived radiactive material into crippled knees can dramatically relieve the pain and swelling of arthritis victims who are not helped by any other treatment, doctors say.

In addition to allowing people to walk again, the researchers hope their experimental therapy will slow or temporarily halt the often relentless destruction caused by rheumatiod arthritis. They believe the treatment is safe.

EXAMPLE #5

Gold containing arthritis implant is adminstered by a hypodermic syringe into the joint or its environs. The gold coated carbon fibers are chopped into very short lengths, approx. 0.020". A slurry is prepared with neutral saline or other body compatible menstruum, and the slurry is injected.

EXAMPLE #6

The slurry of Example #5 comprises a body compatible Silicone Medical grade adhesive, It is well known in medical implantology, a supplier being Dow Chemical Company, Midland Michigan, or its affiliate the Dow-Corning Corp. New York City, N.Y.

EXAMPLE #7

Gold containing arthritis implant comprises Nickel-coated carbon fibers admixed therein. The long term effects of Nickel are not known. Nickel is toxic. It may have a viricidal effect on the newly discovered RA-1 virus that may cause rheumatoid arthritis, according to "SCIENCE" the weekly journal of the American Association for the advancement of Science, Mar. 20, '84. The report was written by Dr. Robert Simpson of the Waksman Institute of Microbiology at Rutgers University and five co-workers at Rutgers, the Eli Lilly Co., and Montefiore Hospital in the Bronx. Date is Mar. 22, 1984.

EXAMPLE #8

Gold containing arthritis implant comprises Silver-coated carbon fibers admixed therein. Silver is moderately toxic. It may have a viricidal effect on Virus RA-1 mentioned in Example #7, above.

Commerical source for the Nickel-coated Carbon Fiber as well as the silver-coated Carbon fiber is the same as the source for the gold coated carbon fiber mentioned above.

EXAMPLE #9

Gold containing arthritis implant comprises carbon fibers coated with alloys of metals, such as Nickel-Silver, or other dissimilar metals ion-implanted discretely on the surface, either of a bare carbon fiber or a pre-coated metal surfaced fiber.

GENERAL DESCRIPTION OF THE INVENTION

In general this invention is a gold containing arthritis implant. It is surgically implanted. It may be injected as a slurry. It may be matted into a pad-like structure. Where other metal integuments are used in this implant, it is not known if the other metals will have any physiological action, but what IS KNOWN is that the efficacy of gold has been well supported in many studies as per the attached from the New England Journal of Medicine, Oct. 27, 1983. X-Ray visualisation of the implant is very easy since Gold is highly radio-opaque, and the Carbon core is radiolucent in comparison. Therefore the pattern of the gold integument on the carbon fiber can be ascertained from time to time and the need for replacement after long-time implant can be determined. The retardation of radiographic deterioration of the joint can be substantiated both in the implanted area and in its environs including bony and tendon structures.

The erose mode of the invention may also be achieved by an imperfectly continuous coating having "windows" as is termed in the electrodeposition art. The reason is to provide galvanic action between the coating and the carbon fiber core, in the ambience of body fluids. The entire invention is a modality for the delivery of gold ions (or other metal ions) from a substantial foundation, by reason of its being a self-contained galvanic couple, of extremely small size, co-acting with the fluids in the body joint. The gold containing arthritis implant can function as a responder to externally applied induction heating energy, creating heat in the highly specific areas of the affected joint, in the areas of the implant.

The advantage perceived in this invention is that it is capable of implantation in extremely small spaces, in the order of a few microns if needed. It can be implanted in the joints of the fingers, the jaw, and in the vertebral spaces. It requires no massive (comparatively) battery and electrical delivery system to generate the ions and to occupy a large space as described within the joint. The gold electrode cannot be pulled down or dimensionally attenuated. It can withstand great compressive and crushing forces as is inherent in its carbon fiber core. Because it exposes both carbon and gold, both widely separated in the electromotive series of elements, it is free to function instantly as a donor of gold wherever body fluid is to be found. It is a galvanic couple.

The specification above and the appended claims are intended to cover all modifications as lie fairly within the spirit and scope of this document, and modifications as will readily occur to those skilled in the art. Thus for example, A slurry of the chopped gold coated Carbon fibers may be used as an oral medicament. A slurry is made in glucose. During the passage through the digestive tract, and in the presence of fluids, each particle acts as a galvanic couple releasing gold ions throughout the entire human system. Their location and concentration are readily determined by X-Ray.

I claim:

1. A joint implant for the continuous production of gold ions to treat the pain of arthritis comprising,
a core element comprising a carbon fiber,
a discontinuous coating of gold on said carbon fiber exposing the carbon in patches,
the carbon fiber and gold forming a galvanic couple which in the presence of body fluids continuously release gold ions to treat the pain of the arthritis.

2. A method of continuously treating arthritis comprising,
providing a core element comprising a carbon fiber,
coating said carbon fiber in a discontinuous manner with gold such that the carbon fiber is exposed in patches,
permanently implanting the thus coated carbon fiber within an arthritic joint,
whereby the gold and carbon fiber form a galvanic couple and in the presence of body fluids continuously release gold ions for relieving the pain of the arthritis.

* * * * *